(12) United States Patent
Jenkins

(10) Patent No.: US 7,182,088 B2
(45) Date of Patent: Feb. 27, 2007

(54) ARM IMMOBILIZER

(75) Inventor: Karen E. Jenkins, Scottsdale, AZ (US)

(73) Assignee: Catholic Healthcare West, Phoenix, AZ (US)

( * ) Notice: Subject to any disclaimer, the term of this patent is extended or adjusted under 35 U.S.C. 154(b) by 13 days.

(21) Appl. No.: 10/738,775

(22) Filed: Dec. 17, 2003

(65) Prior Publication Data

US 2005/0133043 A1     Jun. 23, 2005

(51) Int. Cl.
*A61F 5/37* (2006.01)

(52) U.S. Cl. .................. 128/878; 128/DIG. 6; 604/174; 604/179

(58) Field of Classification Search .............. 128/877, 128/878, 879, DIG. 6, DIG. 26; 604/174, 604/179; 602/3, 5, 12, 20, 21, 23, 26, 60–64
See application file for complete search history.

(56) References Cited

U.S. PATENT DOCUMENTS

| | | | | |
|---|---|---|---|---|
| 3,693,619 A * | 9/1972 | Williams | ................ | 128/892 |
| 3,703,894 A * | 11/1972 | Galloway et al. | ............. | 602/21 |
| 3,722,508 A | 3/1973 | Roberts | | |
| 3,812,851 A | 5/1974 | Rodriguez | | |
| 4,013,070 A * | 3/1977 | Harroff | ................ | 602/21 |
| 4,290,425 A * | 9/1981 | Helfer et al. | ................ | 128/877 |
| 4,370,976 A * | 2/1983 | Wanchik et al. | .............. | 602/22 |
| 4,425,913 A * | 1/1984 | Lewis | ................ | 128/877 |
| 4,470,410 A * | 9/1984 | Elliott | ................ | 128/877 |
| 4,502,477 A | 3/1985 | Lewis | | |
| 4,854,309 A * | 8/1989 | Elsey | ................ | 602/21 |
| 4,928,678 A * | 5/1990 | Grim | ................ | 602/8 |
| 4,941,479 A * | 7/1990 | Russell et al. | .............. | 128/877 |
| 4,941,480 A * | 7/1990 | McLean et al. | .............. | 128/878 |
| 4,945,925 A | 8/1990 | Garcia | | |
| 5,025,801 A | 6/1991 | Callaway | | |
| 5,069,229 A * | 12/1991 | Kurth | ................ | 128/877 |
| 5,449,339 A * | 9/1995 | Drennan | ................ | 602/23 |
| 5,845,643 A | 12/1998 | Vergano et al. | | |
| 6,216,268 B1 * | 4/2001 | Schleicher | ................ | 2/16 |
| 6,773,411 B1 * | 8/2004 | Alvarez | ................ | 602/27 |

* cited by examiner

*Primary Examiner*—Patricia Bianco
*Assistant Examiner*—Camtu Nguyen
(74) *Attorney, Agent, or Firm*—Jennings Strouss & Salmon PLC; Joseph W Mott

(57) ABSTRACT

An arm immobilizer comprises a closeable sleeve of a compressible material which can be placed around the patient's arm above and below the elbow joint with an opening on the inside of the arm positioned to give access to an intravenous site. One or more stays running the length of the immobilizer prevent excessive flexure movement at the elbow, while the compressible foam permits smaller movements that will not dislodge or impede the operation of the intravenous site and attached tube.

9 Claims, 6 Drawing Sheets

ARM IMMOBILIZER

FIELD OF THE INVENTION

This invention relates generally to the field of arm boards and immobilizers for use with patients receiving intravenous therapy.

BACKGROUND OF THE INVENTION

In intravenous therapy, a needle attached to a tube is placed in the vein of the patient, typically near a limb joint such as the elbow or the upper forearm where veins are accessible, and infusion, transfusion, or other procedures or therapies are performed by drawing or passing fluids through the tube. It is desirable in many instances to support the limb in the vicinity of the IV site to restrict movement. This is particularly true with younger patients, as well as incapacitated or unconscious patients, who might have difficulty maintaining a proper arm position.

A prior practice for immobilizing the arm has been to place a short board or splint along the limb and to secure the limb to the board. Keeping an arm straight in this manner is generally uncomfortable, and often attempts are made to mitigate the discomfort by placing padding in various locations on the splint or board. While some discomfort is thereby alleviated, stiffness and aching usually remain.

Other approaches have recognized that the natural position of the arm is not straight at the elbow but presents an angle. Thus, arm boards in a more natural shape have been tried. For example, in U.S. Pat. No. 3,722,508 to Roberts, a plastic arm immobilizer is in a shape of a U-shape channel which itself is contoured to be complimentary to the shape of an arm in the vicinity of the elbow. In another approach, shown in U.S. Pat. No. 3,812,851 to Rodriguez, a slightly flexible arm support allowing limited elbow movement is provided. This immobilizer includes a panel overlying the forearm and a support panel underlying the upper arm, with the panels being joined by a flexible spiral section allowing limited flexure between the two panels.

All of these solutions rely upon rigid materials, either molded plastic contoured shapes or wooden planks, to immobilize the arm. While the contoured plastic versions might be less uncomfortable than a straight splint, their effectiveness depends upon how well they match with the natural curvature of the particular patient's arm. Consequently, a number of different sized and shaped immobilizers would have to be in inventory in order to have one that fits a particular patient. It is an objective of the present invention to provide a comfortable, slightly flexible arm immobilizer that can be used with a wide variety of arm sizes.

SUMMARY OF THE INVENTION

The current invention comprises a closable sleeve of a compressible material, such as foam, which can be placed around the patient's arm above and below the elbow joint with an opening on the inside of the arm positioned to give access to the intravenous site. One or more stays running the length of the immobilizer prevent excessive flexure movement at the elbow, while the compressible foam permits smaller movements that will not dislodge or impede the operation of the intravenous site and attached tube. One or more fasteners may be used to close the sleeve and secure it to the arm of the patient.

DETAILED DESCRIPTION OF THE INVENTION

Figure 1:
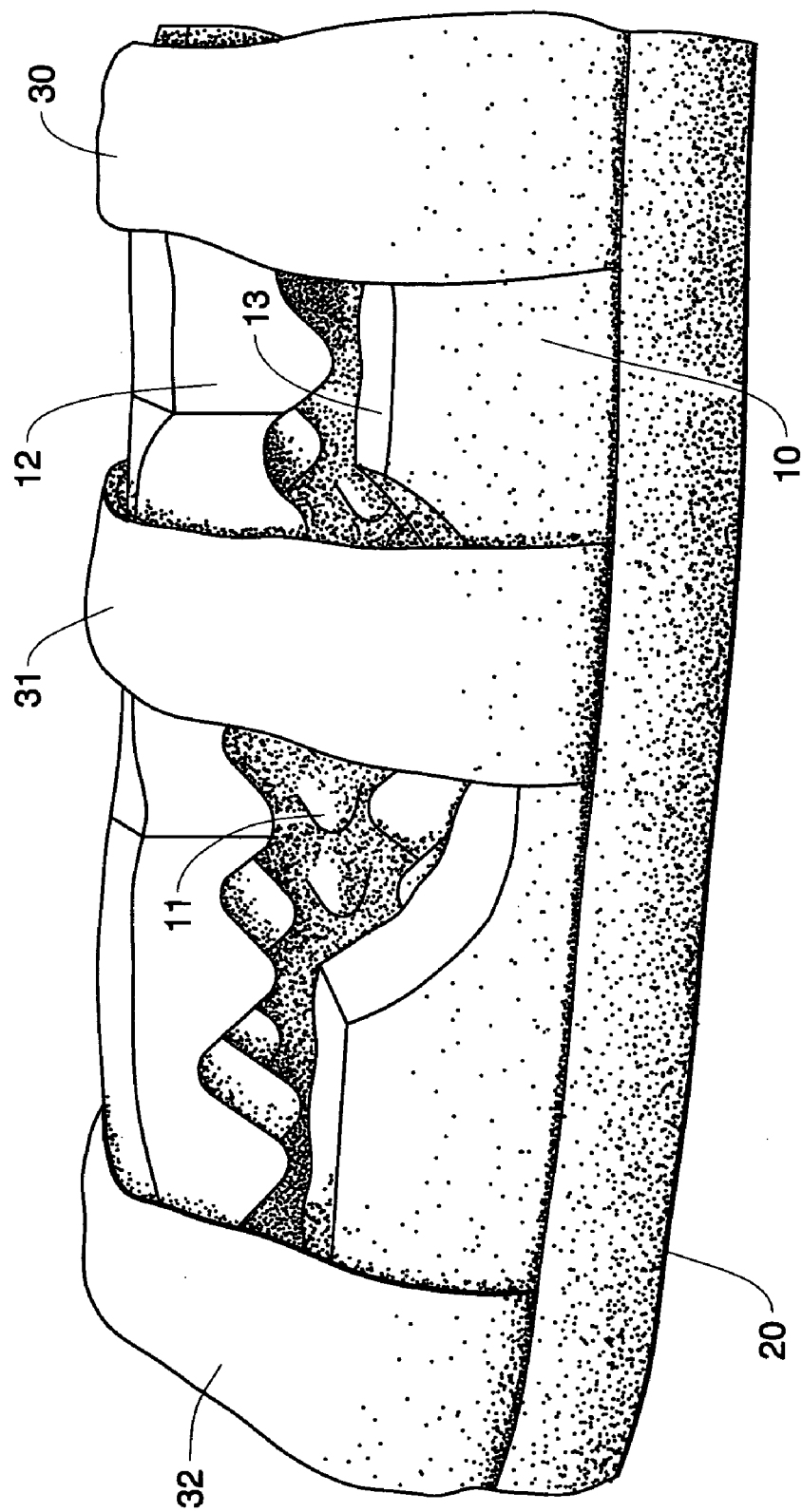
FIG. 1 is an illustration of an embodiment of the immobilizer sleeve of the present invention in a closed position.
Figure 2:
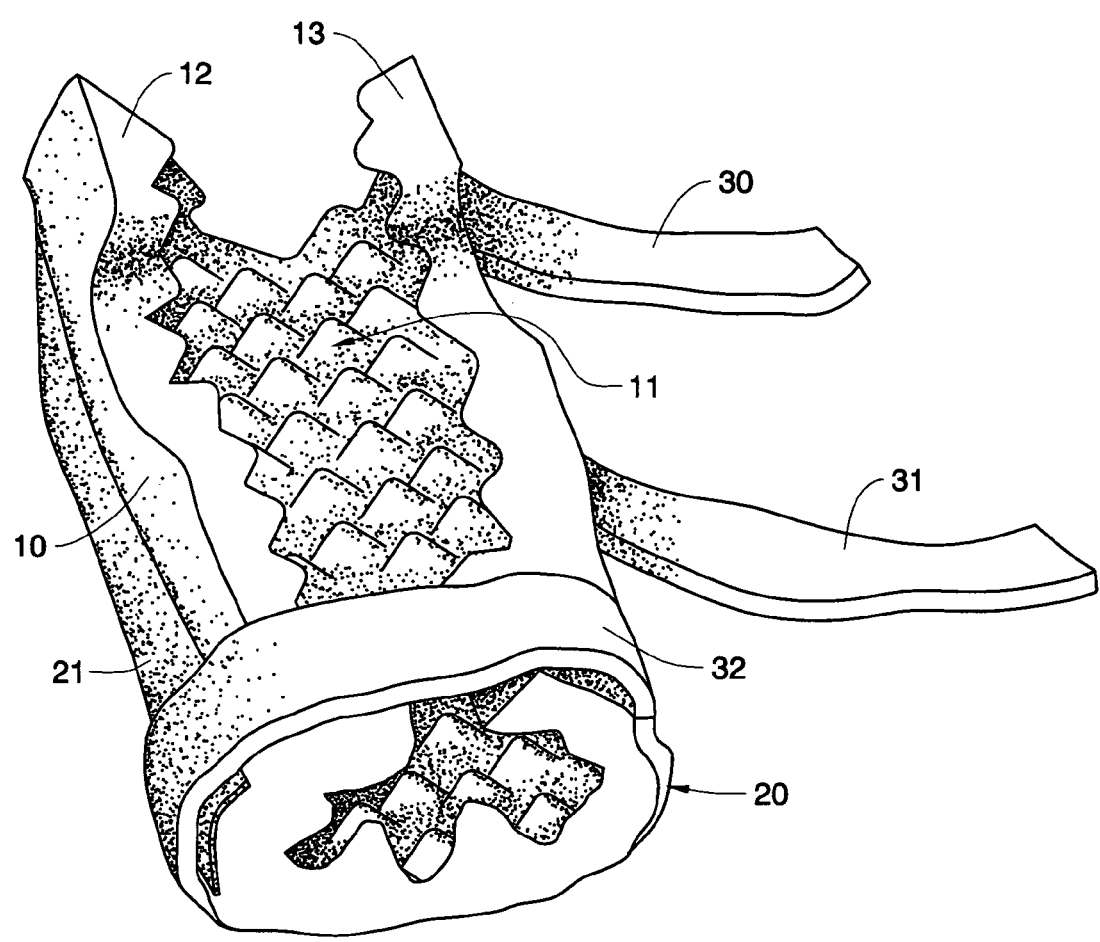
FIG. 2 shows an embodiment of the immobilizer sleeve partially closed, with one of its fasteners in place.

The basic form of the arm immobilizer of the present invention is a closeable sleeve. As used herein, the term refers to a piece of material that will be wrapped around the arm as a sleeve, covering from about the middle of the forearm to about the middle of the upper arm. The preferred shape is rectangular, but other shapes may also work. The sleeve is closeable in that the sleeve sides are wrapped around the arm and secured to each other, thereby securing the sleeve to the arm; it may readily be seen that the sleeve is also "openable" when already attached to the arm. A closed version of the immobilizer sleeve is shown in FIG. 1 and a partially closed view thereof is shown in FIG. 2. The sleeve body 10 is made of a compressible material, preferably a compressible foam, which may be polyurethane, latex or any other standard foam material. More preferably, the sleeve is made of convoluted open cell foam, which is generally known to be less irritating than most materials when applied for long periods against the skin. The overall length of the immobilizer sleeve is sufficient to run from approximately the middle of the inside upper arm to the middle of the forearm of a patient. For an average adult male, this length would be 12 inches to 15 inches.

Figure 3:
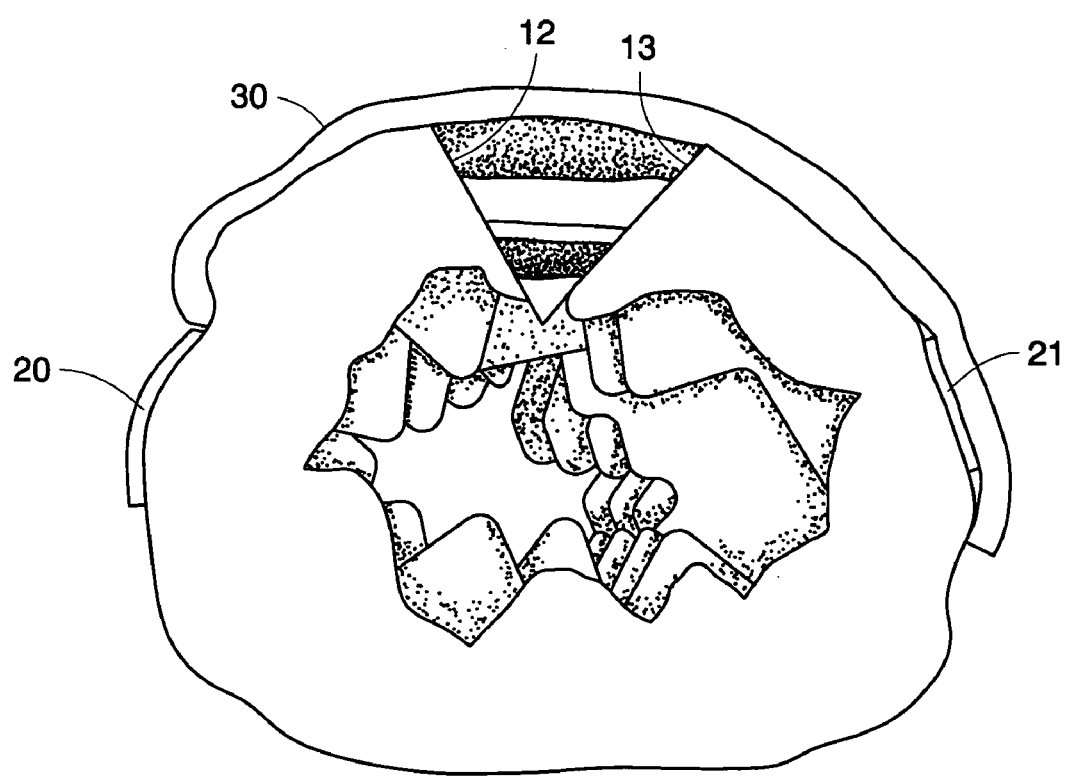
FIG. 3 is an end-on view of the immobilizer of FIGS. 2 and 3.

FIG. 3 shows an end-on view of the immobilizer sleeve in a closed position. The inside diameter of the immobilizer should be approximately matched to the outside diameter of the arm to which it is applied. Where the sleeve material is highly compressible, such as with convoluted open cell foam, the nominal inside diameter may be as small as 2 inches and still accommodate an arm with a 4-inch diameter forearm and 5 to 6-inch diameter upper arm. In the illustrated embodiment, it is not necessary to bring the sides of the open sleeve, 12, 13 into touching connection when the sleeve is closed. The configuration of cross strips, described below, allows for snug fit and adequate immobilizing support in the closed position even when there is a substantial gap between ends 12 and 13.

An immobilizer sleeve for a child would have dimensions smaller than those referenced above. But the relative dimensions would still be an overall length running from mid-forearm to the middle of the upper arm, with an inside diameter (when closed) to snugly accept the patient's upper and lower arm. Given the variations in patient arm dimensions, it may be advisable for a hospital or health care facility to stock several different sizes (e.g., infant; child; small, medium and large adult).

As can be seen in FIGS. 1 and 2, an opening 11 made by cutting out or widening a segment of the sides that will be brought together is provided. This opening is large enough to assure access to the site of the IV insertion in the arm even if the closed sleeve in place brings the two sides 12, 13 into touching connection. It is generally anticipated that the opening will be used for observing the condition of the IV site while the sleeve is in place, and that the sleeve will be removed before changes to the IV are undertaken, but some manipulation of the IV can be accomplished through the opening.

Figure 4:
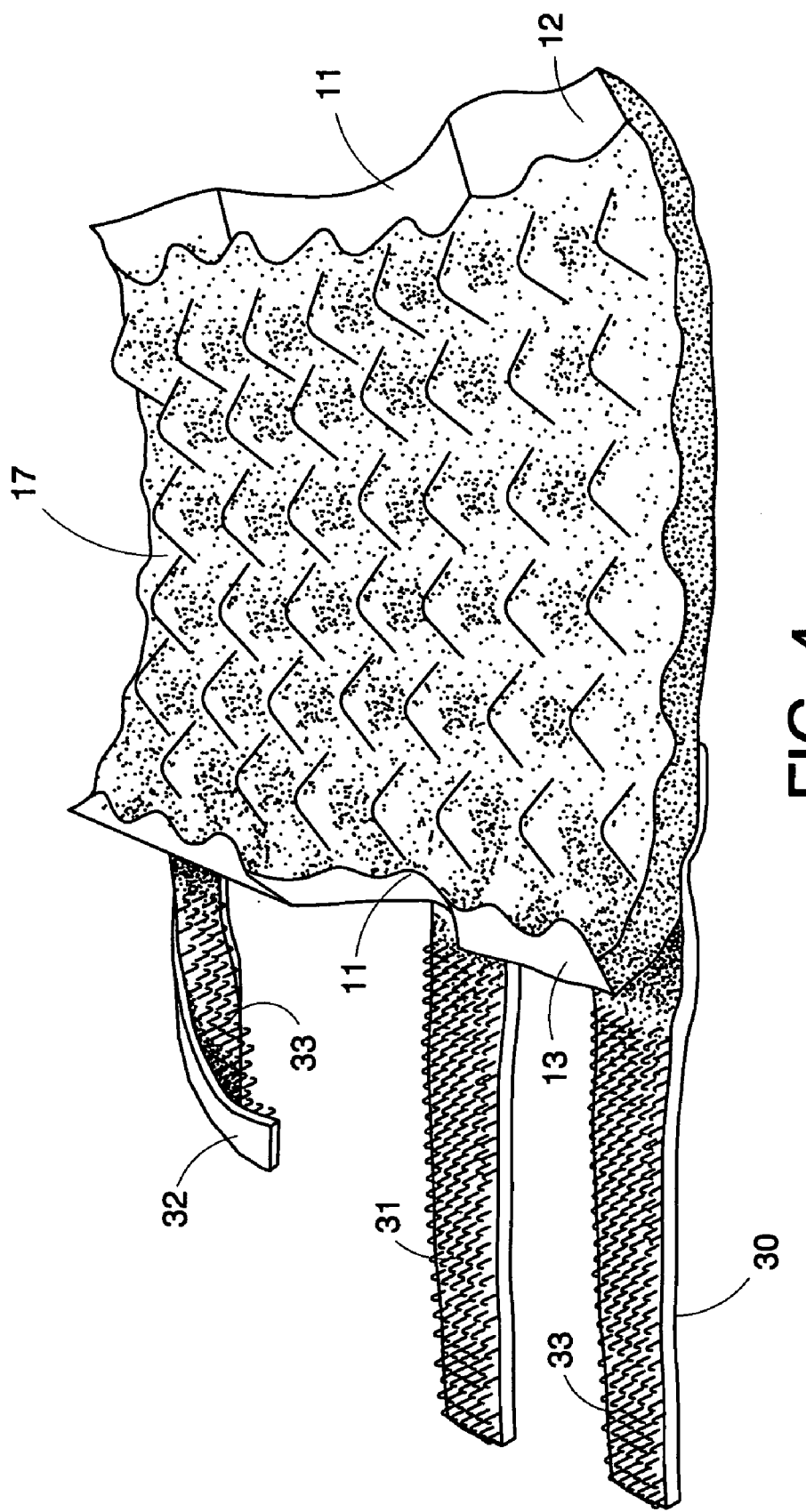
FIG. 4 is a fully open view of the immobilizer sleeve, showing the side that will contact the patient's arm.
Figure 5:
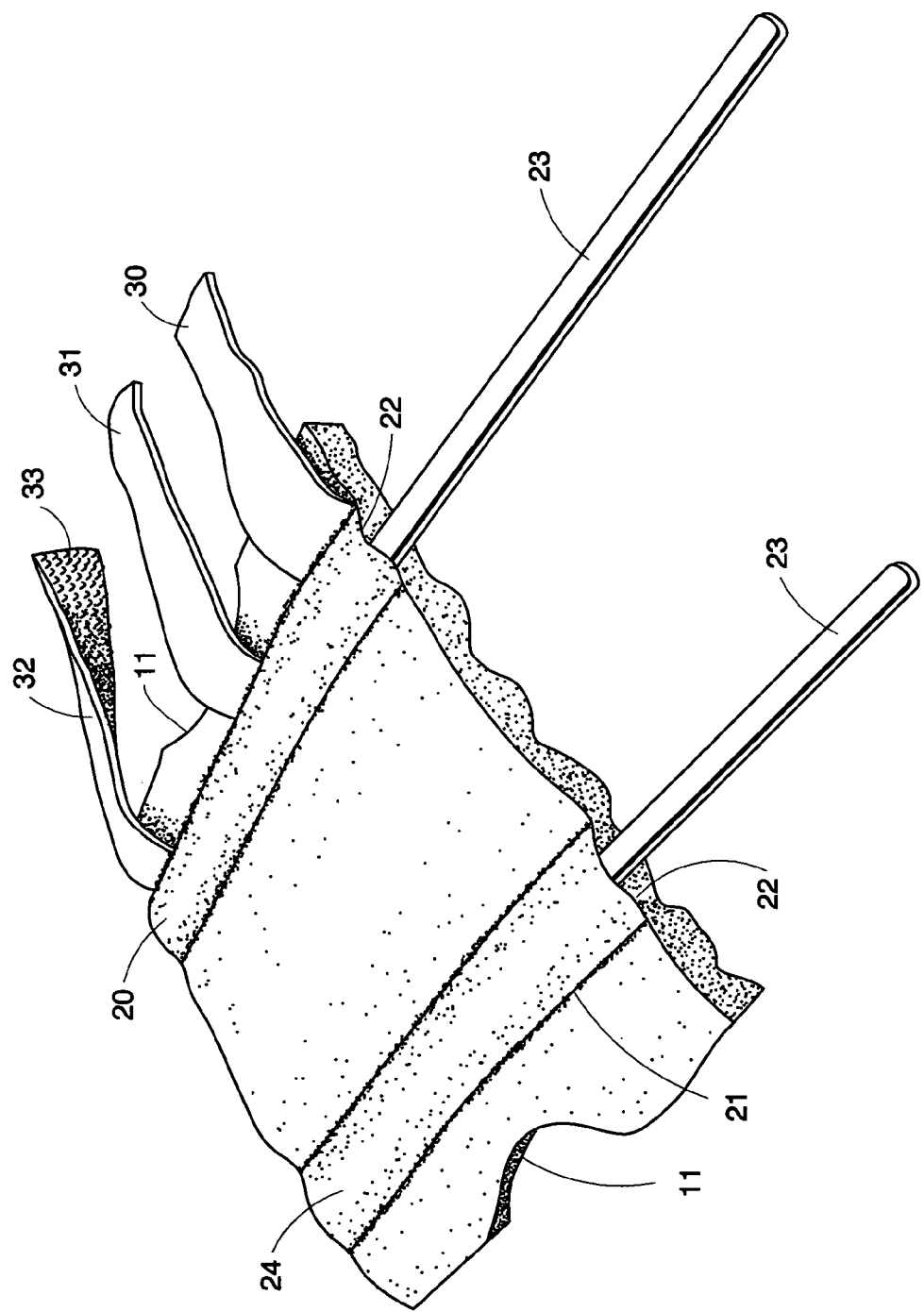
FIG. 5 shows the outside surface of the open sleeve, and includes a pair of steel stays pulled out from the sleeve for illustrative purposes.

A view of the immobilizer sleeve laid open and face up is shown in FIG. 4 and a face down view is shown in FIG. 5. The convoluted foam 17 is clearly seen in FIG. 4. In the FIG. 5 embodiment, the cross width (which forms the outside surface when the sleeve is closed) is approximately 13 inches, corresponding to a closed diameter of about 4 inches. Two longitudinal reinforcing strips 20, 21 are shown, and these are placed so that they will be positioned on either side of the arm when the sleeve is wrapped around the arm and closed down the center of the inner forearm.

The reinforcing strips 20, 21 are tightly woven cotton batting sewn onto the foam material of the sleeve body 10. Each strip has a narrow pocket 22 that runs its entire length. Longitudinal support members 23 are inserted into these pockets. In this embodiment, the reinforcing members are thin steel stays that are about 12 inches long, 2 inches wide, and 10 millimeters thick, and are shown outside the pockets for illustration. Other kinds of longitudinal support members may also be used, and can be attached to or joined with the sleeve material in a variety of ways. The longitudinal support member may be slightly bendable, as illustrated, or unbendable, so that there is a nearly rigid frame or skeleton along the length of the arm, and arm movement is mainly limited to that permitted by compression or distortion of the material of the sleeve body.

In the illustrated embodiment, a strip of material 24 containing the eye loops from a hook-and-eye fabric attachment system, such as the one sold under the trademark Velcro, is affixed to longitudinal reinforcement strip 21. Three cross strips of fabric 30, 31, 32 are securely sewn to the reinforcing strip 20 on the opposite side of the sleeve. Attached to the underside or inside of each cross strip is fabric 33 that serves as the hook portion of the hook-and-eye closure system. As may be seen in FIGS. 1 and 2, these cross strips 30, 31, 32 will adhere when their hook fabric 33 is brought into contact with the eye portion 24 on the opposite reinforcing strip 20, serving as a closing strap or fastener and securing the immobilizer sleeve to the arm. The compressibility of the foam material, combined with the variability of the contact point of the closing strap, permits a sleeve of any particular size to fit a variety of patient arm sizes. One skilled in the art will readily understand that the fastener that holds the sleeve closed may take any of a number of forms, such as buttons and buttonholes, straps, belts, hooks, ribbons, snaps, buckles, elastic bands, or any mechanism to hold the ends together (whether touching or not) and the sleeve snugly in place.

Figure 6:
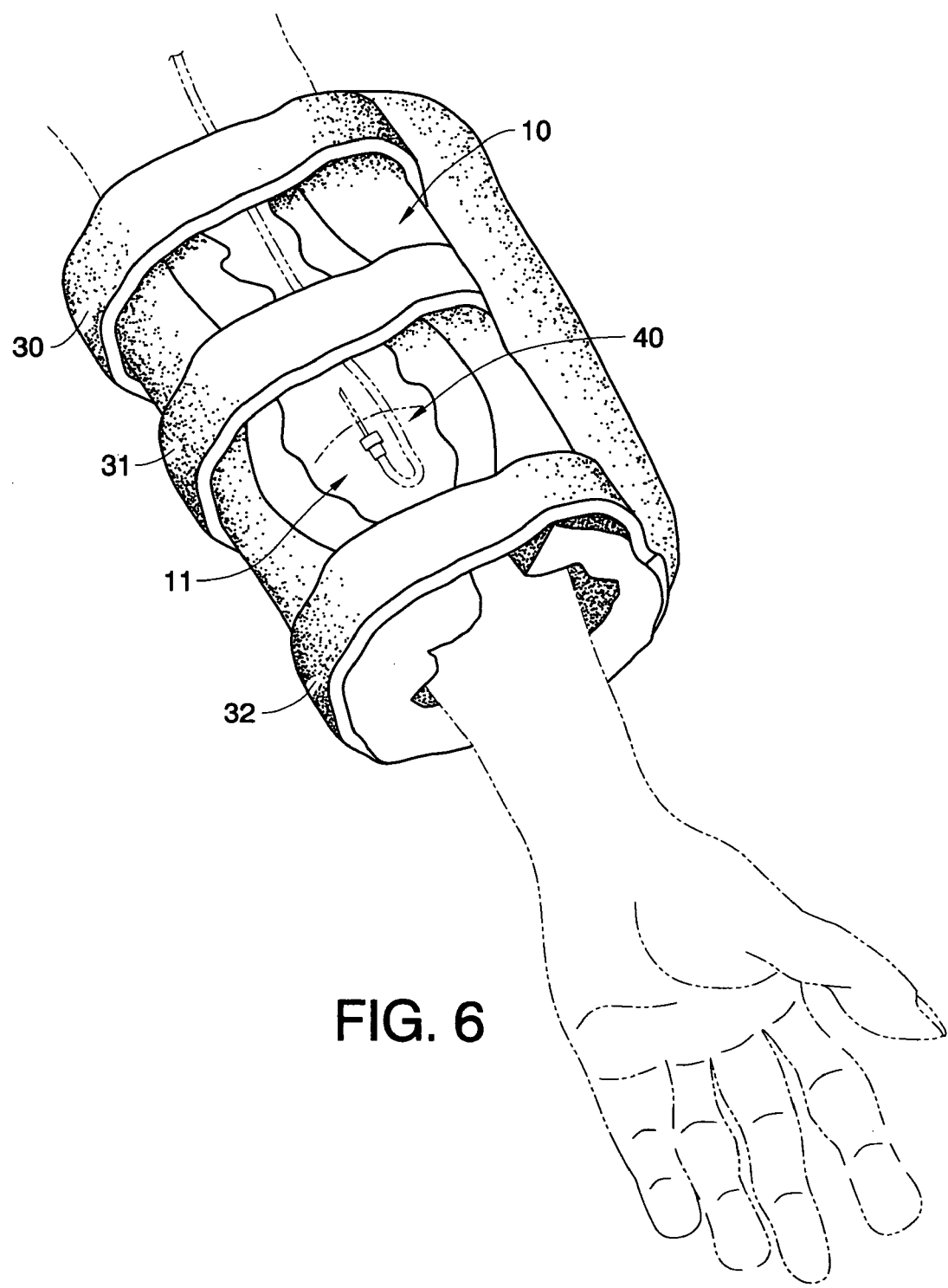
FIG. 6 shows an immobilizer on the arm of a patient having an IV inserted at the antecubital vein.

FIG. 6 shows an immobilizer sleeve 10 in place on a patient's arm (shown in phantom). In this case, the sides of the sleeve abut each other at the closure position, and the cut out opening 11 provides ready access to the intravenous site 40. The patient's arm is relatively but comfortably immobile and the intravenous needle and tubing will not be disturbed by the small motions that the patient is able to make.

While the invention has been illustrated with respect to a particular embodiment thereof, persons of ordinary skill in the art will readily see that variations in materials, dimensions, fasteners and longitudinal support structures may be implemented without departing from the spirit and scope of the invention.

What is claimed is:

1. An arm immobilizer comprising a closeable sleeve of a compressible material having a preformed opening disposed in the approximate center of the sleeve for access to a wearer's intravenous site, at least one lonaitudinal support member and at least one fastener for closing the sleeve on a wearer's arm, wherein an aligned pair of widened segments on opposing sides of the sleeve forms the preformed opening when the sleeve is closed on the wearer's arm.

2. The immobilizer of claim 1, wherein the compressible material is convoluted foam.

3. The immobilizer of claim 1, wherein the fastener comprises a hook and eye closure system with one portion of the system attached to a side of the sleeve and the other portion of the system attached to a cross strip attached to an opposite side of the sleeve.

4. The immobilizer of claim 1, wherein the longitudinal support member comprises a steel stay inserted into a pocket in a reinforcing strip attached lengthwise to the sleeve.

5. The immobilizer of claim 1, wherein the compressible material is foam.

6. An arm immobilizer comprising a closeable sleeve of a compressible material having an opening for access to a wearer's intravenous site formed in the approximate center of the sleeve when the sleeve is closed by an aligned pair of widened segments on opposing sides of the sleeve, a plurality of reinforcing strips attached lengthwise on the sleeve, each strip including a reinforcing strip pocket running along it, a plurality of longitudinal support stays, each of which is inserted in a reinforcing strip pocket, and a plurality of fasteners for closing the sleeve on a wearer's arm.

7. The immobilizer of claim 6 wherein the fastener comprises a hook and eye closure system with one portion of the system attached to a reinforcing strip on one side of the sleeve and the other portion of the system attached to a cross strip attached to a reinforcing strip on an opposite side of the sleeve.

8. The immobilizer of claim 7 wherein the compressible material is convoluted foam.

9. The immobilizer of claim 7 wherein the compressible material is foam.

* * * * *